(12) United States Patent
Hallberg

(10) Patent No.: US 9,208,770 B2
(45) Date of Patent: Dec. 8, 2015

(54) NOISE EVENT SUPPRESSION FOR MONITORING SYSTEM

(71) Applicant: Sharp Laboratories of America, Inc., Camas, WA (US)

(72) Inventor: Bryan Severt Hallberg, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 172 days.

(21) Appl. No.: 14/155,564

(22) Filed: Jan. 15, 2014

(65) Prior Publication Data

US 2015/0199951 A1    Jul. 16, 2015

(51) Int. Cl.
*H04B 15/00* (2006.01)
*G10K 11/16* (2006.01)

(52) U.S. Cl.
CPC ........................................ *G10K 11/16* (2013.01)

(58) Field of Classification Search
CPC .............................. G10K 11/16; G10K 11/175
USPC ........... 381/73.1, 94.1, 94.2, 94.3, 94.4, 94.5, 381/94.6, 94.7, 94.8, 94.9
See application file for complete search history.

(56) References Cited

U.S. PATENT DOCUMENTS

| | | | | |
|---|---|---|---|---|
| 3,700,812 A | * | 10/1972 | Springett | H04B 15/00 381/94.4 |
| 5,119,321 A | * | 6/1992 | Burton, Jr. et al. | H03H 11/04 702/194 |
| 7,050,721 B1 | | 5/2006 | Jansen et al. | |
| 8,189,952 B2 | | 5/2012 | Chen et al. | |
| 8,489,666 B1 | | 7/2013 | Nikitin | |
| 2004/0165736 A1 | * | 8/2004 | Hetherington et al. | G10L 21/0208 381/94.3 |

OTHER PUBLICATIONS

Matlab, "Filtering and Smoothing Data", Nov. 29, 2012.*

* cited by examiner

*Primary Examiner* — Paul S Kim
*Assistant Examiner* — Katherine Faley
(74) *Attorney, Agent, or Firm* — Scot A. Reader

(57) ABSTRACT

A noise event suppression technique for a monitoring system detects a noise event in a signal waveform when a focal sample in the waveform has an amplitude greater than an amplitude of algorithmically determined earlier and later samples in the waveform that are noncontiguous with the focal sample. When the monitoring system detects the noise event, the monitoring system reduces the amplitude of the focal sample to an amplitude between those of the earlier and later samples. The monitoring system outputs data determined using the waveform once noise events have been adequately suppressed.

17 Claims, 6 Drawing Sheets

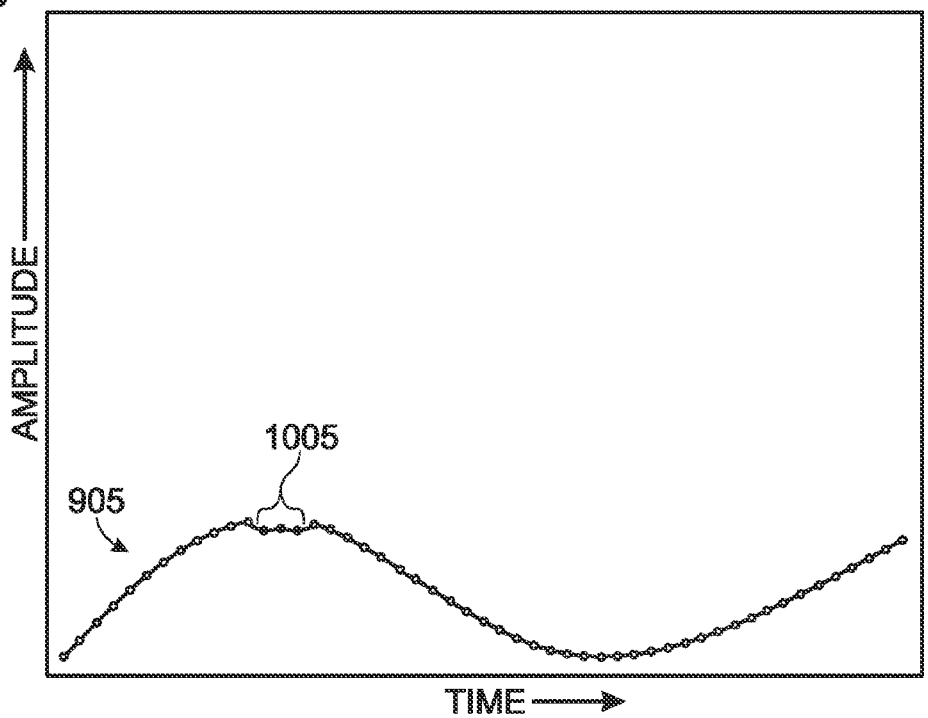
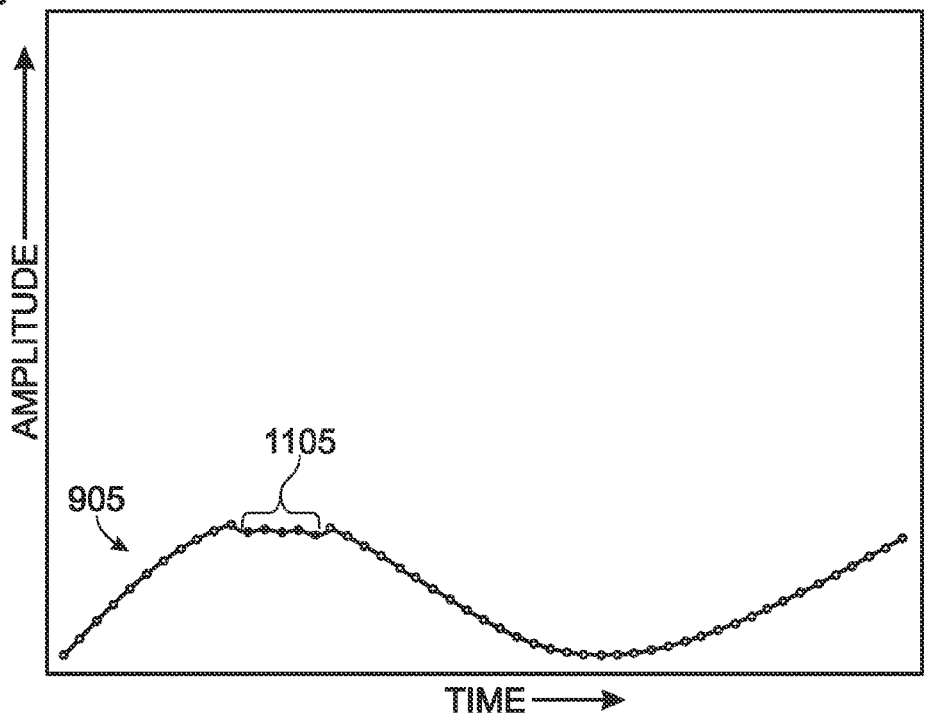

NOISE EVENT SUPPRESSION FOR MONITORING SYSTEM

BACKGROUND OF THE INVENTION

The present invention relates to suppression of noise in signal waveforms.

Monitoring systems, such as personal health monitors, acquire and extract data from signal waveforms. Unfortunately, signal waveforms often exhibit unwanted noise bursts or spikes caused by transient input stimulus. For example, when a microphone of a personal health monitor is mounted on the human body, the microphone may detect abrupt hits, clothing scrapes and other impulse sounds that manifest themselves as noise bursts in a raw acoustic signal waveform. When an acoustic signal energy waveform is computed from the raw waveform, the noise bursts present as noise spikes in the energy waveform which, if not suppressed, can prevent or hinder extraction of reliable data, such as respiration or heart rate data, from the energy waveform.

Many conventional techniques for suppressing noise events in signal waveforms have relied mainly on low-pass frequency or median filtering. These conventional techniques have shortcomings in terms of inadequately suppressing noise events, dramatically degrading signal quality, or both. FIG. 1 shows an exemplary energy waveform exhibiting noise spikes that are inadequately suppressed by conventional filtering. The unfiltered waveform 110 exhibits large amplitude noise spikes. After application of a low-pass filter to waveform 110, the noise spikes are somewhat suppressed, but the low-pass filtered waveform 120 still has noise spikes of moderate amplitude. These noise spikes could perhaps be further reduced by applying a low-pass filter covering a narrower band, but applying a narrower band low-pass filter would remove a substantial portion of the signal of interest, reducing its amplitude and distorting its shape. Similarly, application of a median filter to unfiltered waveform 110 results in a median filtered waveform 130 that continues to have moderate amplitude noise spikes. These noise spikes could perhaps be further reduced by applying a median filter of larger sample size, but applying a larger sample size median filter would further degrade the quality of the signal of interest by reducing signal resolution. Moreover, applying a median filter, regardless of sample size, raises the noise floor in the signal since the samples that exhibit large noise are part of the sample group used to identify the median samples.

SUMMARY OF THE INVENTION

The present invention provides a noise event suppression technique for a monitoring system which adequately suppresses noise events in a signal waveform without having to apply a narrow band low-pass filter or a median filter that dramatically degrades signal quality or raises the noise floor in the signal. In the instant technique, a monitoring system detects a noise event in a signal waveform when a focal sample in the waveform has an amplitude greater than an amplitude of both algorithmically determined earlier and later samples in the waveform that are noncontiguous with the focal sample. When the monitoring system detects the noise event, the monitoring system reduces the amplitude of the focal sample to an amplitude between those of the earlier and later samples. The monitoring system outputs data determined using the waveform once noise events have been adequately suppressed through the foregoing technique.

In one aspect of the invention, a method for suppressing noise events in a signal waveform having a plurality of samples comprises acquiring by a monitoring system the waveform; selecting by the monitoring system from the plurality of samples a focal sample; determining algorithmically by the monitoring system from the plurality of samples a discrete sample earlier than the focal sample and a discrete sample later than the focal sample that are noncontiguous with the focal sample; determining by the monitoring system whether the focal sample has an initial amplitude greater than an amplitude of the discrete earlier sample and greater than an amplitude of the discrete later sample; reducing by the monitoring system the initial focal sample amplitude to a reduced focal sample amplitude between the earlier and later sample amplitudes in response to determining that the initial focal sample amplitude is greater than the earlier and later sample amplitudes; and outputting by the monitoring system data determined using the waveform.

In some embodiments, the first determining step comprises identifying a current sample group consisting of the focal sample, one or more samples earlier than the focal sample that are contiguous with the focal sample and one or more samples later than the focal sample that are contiguous with the focal sample; identifying an earlier sample group consisting of the discrete earlier sample and two or more additional samples that are earlier than the current sample group; identifying a later sample group consisting of the discrete later sample and two or more additional samples that are later than the current sample group; determining that the discrete earlier sample is a median amplitude sample of the earlier sample group; and determining that the discrete later sample is a median amplitude sample of the later sample group.

In some embodiments, the earlier, current and later sample groups each consist of an odd number of samples.

In some embodiments, the earlier, current and later sample groups consist of a number of samples selected to correspond with a predetermined target width of noise spikes to be suppressed.

In some embodiments, the method further comprises determining by the monitoring system that a slope between at least two consecutive samples within one or more of the earlier, current or later sample group exceeds a configurable threshold.

In some embodiments, the reduced focal sample amplitude is linearly interpolated from the earlier sample amplitude and the later sample amplitude.

In some embodiments, the reduced focal sample amplitude is nonlinearly interpolated from the earlier sample amplitude and the later sample amplitude.

In some embodiments, the reduced focal sample amplitude is computed as an average of the earlier sample amplitude and the later sample amplitude.

In some embodiments, the method further comprises, after the reducing step, selecting by the monitoring system other samples within the plurality of samples of the waveform as the focal sample and performing by the monitoring system at least the determining steps for the other samples as the focal sample.

In some embodiments, the method further comprises, after the performing step, reselecting by the monitoring system each of the samples within the plurality of samples of the waveform as the focal sample and reperforming by the monitoring system at least the determining steps for each of the samples as the focal sample.

In some embodiments, the signal waveform is an acoustic signal waveform.

In some embodiments, the outputted data comprise respiration data.

In some embodiments, the outputted data comprise heart data.

In another aspect of the invention, a monitoring system comprises a signal capture element configured to acquire a signal waveform comprising a plurality of samples; a signal processing element operatively coupled with the capture element and configured to select from the plurality of samples a focal sample, determine algorithmically from the plurality of samples a discrete sample earlier than the focal sample and a discrete sample later than the focal sample that are noncontiguous with the focal sample, determine whether the focal sample has an initial amplitude greater than an amplitude of the discrete earlier sample and greater than an amplitude of the discrete later sample and reduce the initial focal sample amplitude to a reduced focal sample amplitude between the earlier and later sample amplitudes in response to determining that the initial focal sample amplitude is greater than the earlier and later sample amplitudes; and a data output interface operatively coupled with the processing element and configured to output data determined using the waveform.

In yet another aspect of the invention, a method for suppressing noise events in a bipolar signal waveform having a plurality of samples comprises acquiring by a monitoring system the waveform; selecting by the monitoring system from the plurality of samples a focal sample; determining algorithmically by the monitoring system from the plurality of samples a discrete sample earlier than the focal sample and a discrete sample later than the focal sample that are noncontiguous with the focal sample; determining by the monitoring system an absolute value of an initial amplitude of the focal sample, an absolute value of an amplitude of the discrete earlier sample and an absolute value of an amplitude of the discrete later sample; determining by the monitoring system whether the absolute value of the initial focal sample amplitude is greater than the absolute value of the discrete earlier sample amplitude and greater than the absolute value of the discrete later sample amplitude; changing by the monitoring system the initial focal sample amplitude to a modified focal sample amplitude between the earlier and later sample amplitudes in response to determining that the absolute value of the initial focal sample amplitude is greater than the absolute values of the earlier and later sample amplitudes; and outputting by the monitoring system data determined using the waveform.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 10 illustrates reduction of a focal sample amplitudes in the waveform of FIG. 9 to reduced focal sample amplitudes pursuant to application of the method to the waveform in a first iteration.

FIG. 11 illustrates further reductions of focal sample amplitudes in the waveform of FIG. 9 to reduced focal sample amplitudes pursuant to application of the method to the waveform in second and third iterations.

DETAILED DESCRIPTION OF A PREFERRED EMBODIMENT

Figure 1:
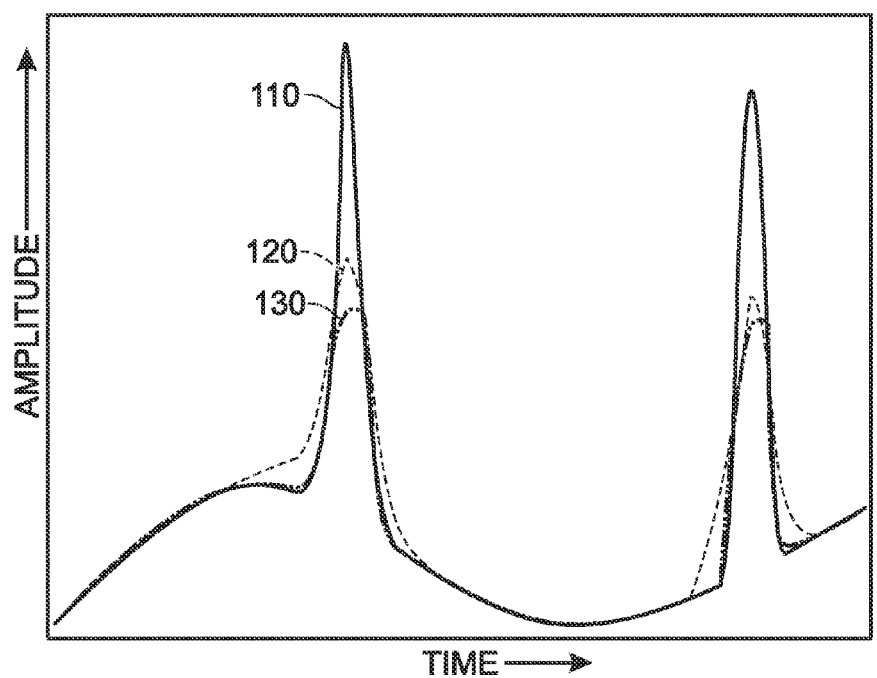
FIG. 1 shows a noisy acoustic signal energy waveform before and after conventional low pass and median filtering.
Figure 2:
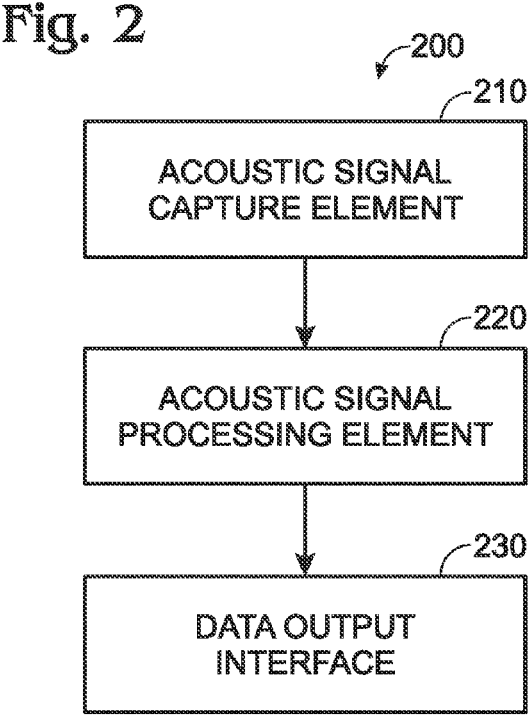
FIG. 2 shows an acoustic monitoring system in some embodiments of the invention.

FIG. 2 shows an acoustic monitoring system 200 in some embodiments of the invention. Monitoring system 200 includes an acoustic signal capture element 210, an acoustic signal processing element 220 and a data output interface 230, which are communicatively coupled in series.

Capture element 210 includes a sound transducer, such as a microphone, that continually detects sounds, generates digital samples that reflect detected sounds and transmits the digital samples one at a time to processing element 220. Capture element 210 may include one or more amplifiers, frequency filters and an analog/digital converter to facilitate in generating and removing noise in digital samples. The digital samples have varying amplitudes representing sounds of interest as well as noise. Sounds of interest are sounds indicative of parameters to be monitored by monitoring system 200.

Processing element 220 receives the digital samples from capture element 210 and generates raw acoustic signal waveforms each having a configurable number of digital samples. The raw waveforms are a time series of digital samples of varying amplitudes. Impulse noise manifests itself as noise bursts in the raw waveforms. Processing element 220 computes a time series of acoustic signal energy waveforms corresponding to the raw waveforms and caches the energy waveforms in a signal buffer on processing element 220.

At a given time, the signal buffer holds an energy waveform having a configurable number of digital samples describing energy in the acoustic signal during a particular time window. The samples in the energy waveform have varying amplitudes representing detected sounds of interest as well as detected noise. Impulse noise manifests itself as noise spikes in the energy waveform. Processing element 220 suppresses the noise spikes by performing a noise event suppression technique described herein. Once noise spikes in the energy waveform are adequately suppressed, processing element 220 extracts parametric data from the energy waveform and transmits the parametric data to output interface 230. In some embodiments, processing element 220 performs its indicated functions under control of a microprocessor executing software instructions. In other embodiments, processing element

220 may perform its indicated functions in whole or in part using a microcontroller or custom circuitry.

Output interface 230 has a display screen for displaying parametric data received from processing element 220 and information derived from such data. In some embodiments, output interface 230, in addition to a display screen, has a communication interface to an internal or external data management system that stores parametric data and derivative information and/or a communication interface that transmits such data and information to a remote monitoring device.

In some embodiments, capture element 210, processing element 220 and output interface 230 are communicatively coupled over wired communication links. In other embodiments, at least two of capture element 210, processing element 220 or output element 230 are communicatively coupled over wireless communication links.

In some embodiments, monitoring system 200 is a personal health monitor. In these embodiments, capture element 210 includes a microphone positioned on the body of a person being monitored, such as the chest, back, or neck, which continually detects physiological sounds, such as respiration and heart sounds, emanating from the monitored person. Capture element 210 generates digital samples expressing detected physiological sounds and transmits the digital samples one at a time to processing element 220. The digital samples have varying amplitudes representing physiological sounds of interest as well as noise. The sounds of interest are sounds indicative of physiological parameters to be monitored by the personal health monitor, such as respiration rate and/or heart rate. Capture element 210 transmits the digital samples to processing element 220 which generates acoustic signal energy waveforms from the digital samples. Once processing element 220 through application of the noise suppression technique described herein adequately suppresses noise spikes in the energy waveforms, processing element 220 extracts physiological parametric data from the energy waveforms, such as respiration rate and heart rate, and transmits the physiological parametric data to output interface 230. Output interface 230 has a display screen for displaying physiological parametric data received from processing element 220 and information derived from such data, such as numerical scores or color-coded indicators. In some embodiments, output interface 230, in addition to a display screen, has a communication interface to an internal or external data management system that stores the physiological parametric data and derivative information and/or a communication interface that transmits such data and information to a remote monitoring device, such as a monitoring device at a clinician facility.

Figure 3:
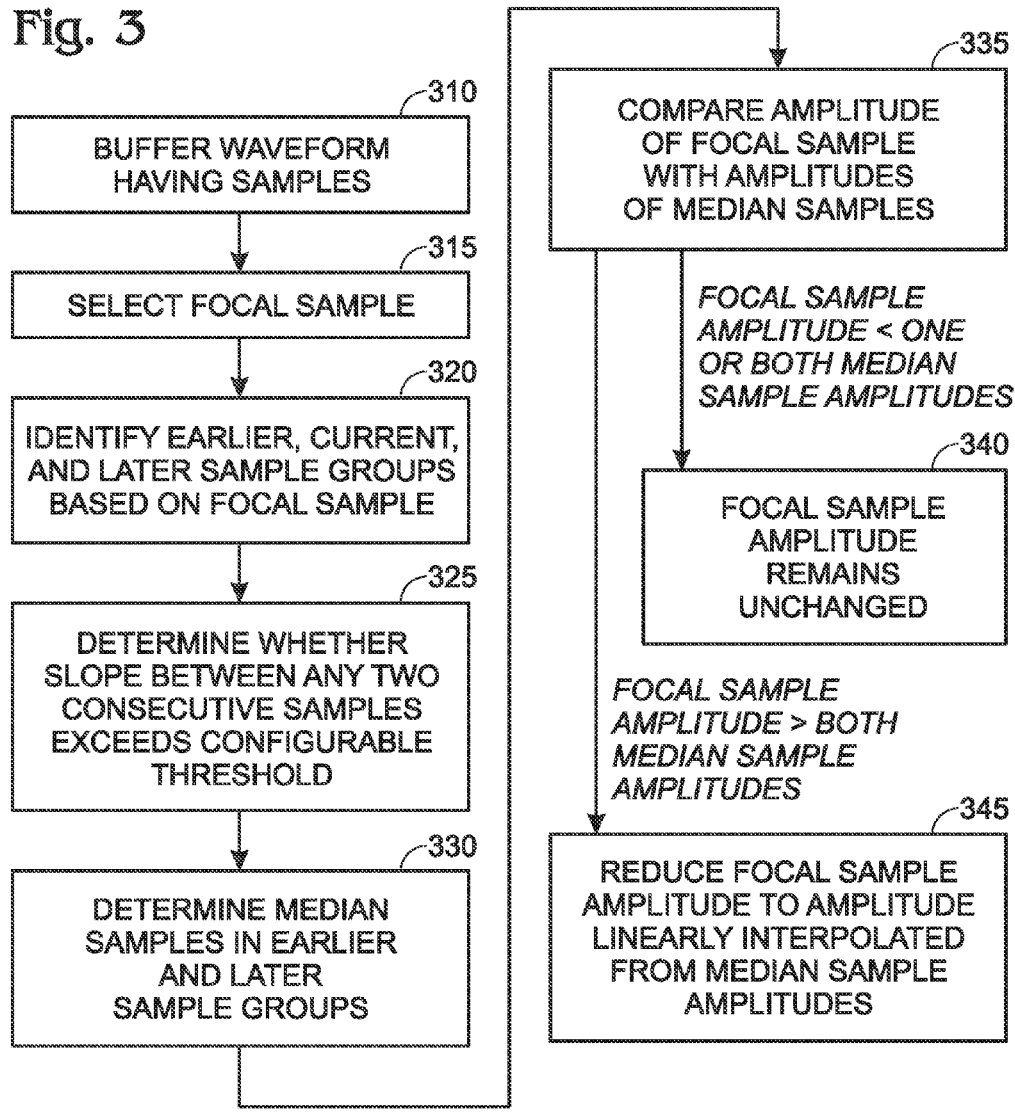
FIG. 3 shows a method for suppressing noise events in an acoustic signal waveform in some embodiments of the invention.

FIG. 3 shows a method for suppressing noise events in an acoustic signal waveform in some embodiments of the invention. The method is performed by processing element 220.

At the outset, processing element 220 buffers in a signal buffer on processing element 220 an acoustic signal energy waveform having a configurable number of digital samples (310).

Processing element 220 next selects a focal sample from the buffered waveform (315). Focal samples are judiciously selected to ensure there is a sufficient number of samples in the buffered waveform earlier and later than the focal sample to enable identification of both an earlier and later sample group as described herein. In some embodiments, the method is performed on a buffered waveform in multiple iterations. The initial focal sample in each iteration is the earliest sample in the buffered waveform that permits an earlier sample group to be formed and the final focal sample in each iteration is the latest sample in the buffered waveform that permits a later sample group to be formed.

Figure 4:
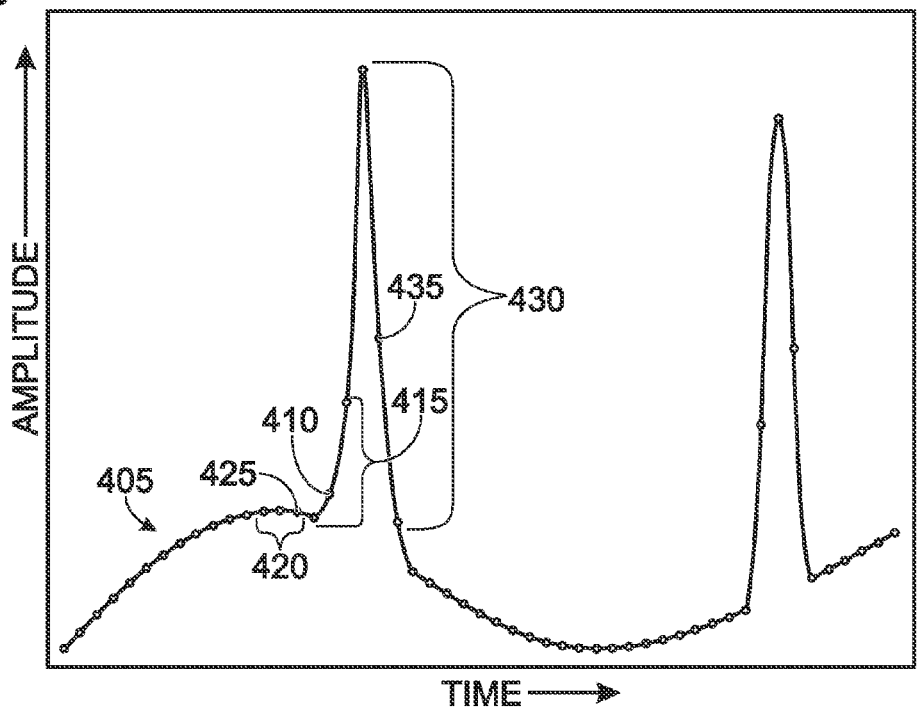
FIG. 4 illustrates identification of earlier, current and later sample groups in a noisy acoustic signal waveform based on a focal sample.

Processing element 220 next determines algorithmically a discrete sample earlier than the focal sample and a discrete sample later than the focal sample that are noncontiguous with the focal sample. Once determined, these samples are used in amplitude comparisons with the focal sample indicative of whether the focal sample is or is not part of a noise spike. In making the algorithmic determination, processing element 220 first identifies earlier, current and later sample groups by keying off the focal sample (320). The earlier, current and later sample groups are characterized by an odd number of samples, with the earlier and later sample groups consisting of the same odd number. In some embodiments, the earlier, current and later groups each consist of at least three samples. The earlier, current and later sample groups are further characterized by contiguity with one another. In some embodiments, the current sample group consists of the focal sample as its center sample as well as at least one earlier sample and at least one later sample that are contiguous with the focal sample. The earlier sample group consists of at least three samples that are earlier than and contiguous with the current sample group. The later sample group consists of at least three samples that are later than and contiguous with the current sample group. Moreover, in some embodiments, the number of samples in the earlier, current and later sample groups is selected in accordance with a predetermined target width of noise spikes to be suppressed. For example, the number of samples in the sample groups may be selected such that at least one focal sample on a noise spike having the predetermined target width will have an amplitude greater than the amplitude of a median sample in the earlier sample group and greater than the amplitude of a median sample in the later sample group. Identification of the earlier, current and later sample groups may be better understood by reference to FIG. 4. There, a buffered waveform 405 has a current sample group 415 consisting of the focal sample 410 as the center sample as well as an earlier sample and later sample that are contiguous with focal sample 410. Buffered waveform 405 further has an earlier sample group 420 consisting of the three samples that are earlier than and contiguous with current sample group 415, and a later sample group 430 consisting of the three samples that are later than and contiguous with current sample group 415.

Processing element 220 next determines whether a slope between any two consecutive samples in the identified earlier, current and later sample groups exceeds a configurable threshold (325). If the slope between no two consecutive samples spanning from the earliest sample in the earlier sample group and the latest sample in the later sample group exceeds the configurable threshold, the focal sample is presumed not to be part of a noise spike and any reduction of the focal sample pursuant to application of the noise suppression method will degrade signal quality unnecessarily. In that event, the remaining steps of the suppression method are not applied to the current focal sample and the focus shifts to the next sample. On the other hand, if the slope between at least two consecutive samples spanning from the earliest sample in the earlier sample group and the latest sample in the later sample group exceeds the configurable threshold, application of the nose suppression method to the current focal sample continues. In some embodiments, the threshold is configured based on the amplitude and width of noise spikes in the buffered waveforms measured relative to a baseline amplitude such as average signal amplitude, median signal amplitude or the noise floor. Returning to FIG. 4, for buffered waveform 405 the threshold is configured such that the slope between at least two consecutive samples spanning from the earliest sample in earlier sample group 420 and the latest sample in the later sample group 430 exceeds the threshold and application of the noise suppression method to focal sample 410 proceeds.

Provided the slope between at least two consecutive samples spanning from the earliest sample in the earlier sample group and the latest sample in the later sample group exceeds the configurable threshold, processing element 220 proceeds to identify the median samples in the identified earlier and later sample groups (330). The median samples are the samples of median amplitude within their respective groups. Returning to FIG. 4, processing element 220 identifies sample 425 within earlier sample group 420 and sample 435 within later sample group 430 as median samples.

Processing element 220 next individually compares the amplitude of the focal sample with the amplitudes of the median samples of the earlier and later sample groups (335). In this regard, if the amplitude of the focal sample is greater than the amplitude of the median sample of earlier sample group and also greater than the amplitude of the median sample of the later sample group, the focal sample is presumed to be part of a noise spike in the buffered waveform. Returning to FIG. 4, processing element 220 compares the amplitude of focal sample 410 with the amplitude of median sample 425 and separately compares the amplitude of focal sample 410 with the amplitude of median sample 435 to assess whether focal sample 410 is part of a noise spike in buffered waveform 405.

Processing element 220 next follows one of two conditional branches based on the outcome of the amplitude comparisons. If the amplitude of the focal sample is less than either the amplitude of the median sample of the earlier sample group or the amplitude of the median sample of the later sample group, or both, the focal sample is presumed not to be a part of a noise spike in the buffered waveform and is left unchanged (340). For example, returning to FIG. 4, the amplitude of focal sample 410 is greater than the amplitude of median sample 425 but less than the amplitude of media sample 435, such that the amplitude of focal sample 410 is left unchanged.

Figure 5:
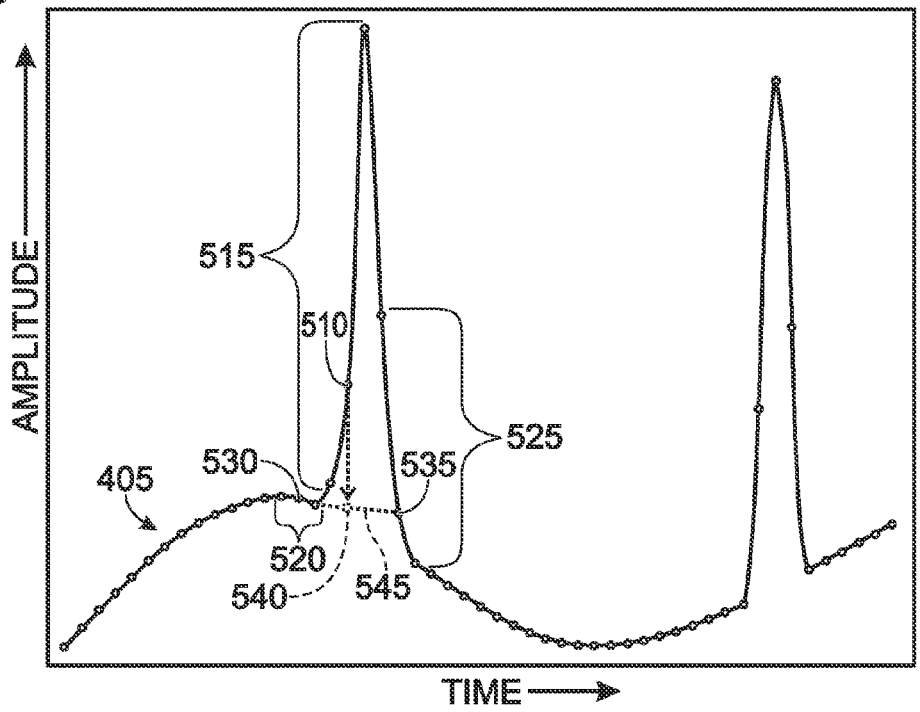
FIG. 5 illustrates a reduction of an initial focal sample amplitude in the waveform of FIG. 4 to a reduced focal sample amplitude pursuant to application of the method to the focal sample in a first iteration.

On the other hand, if the amplitude of the focal sample is greater than both the amplitudes of the median samples of the earlier and later sample groups, the focal sample is presumed to be a part of a noise spike in the buffered waveform and is reduced to an amplitude linearly interpolated from the median sample amplitudes (345). The focal sample amplitude reduction performed in Step 345 may be better understood by reference to FIG. 5, where the focus has shifted from focal sample 410 to the next focal sample 510 in buffered waveform 405. As shown in FIG. 5, processing element 220 has identified current sample group 515, earlier sample group 520 and later sample group 525 by keying off focal sample 510. Processing element 220 has also determined that a slope between at least two consecutive samples in the identified sample groups 515, 520, 525 exceeds a configurable threshold and identified median samples 530, 535 in the earlier sample group 520 and later sample group 525, respectively. Processing element 220 has further individually compared the amplitude of focal sample 510 with the amplitudes of median samples 530, 535 and determined that the amplitude of focal sample 510 is greater than both of the amplitudes of median samples 530, 535. Accordingly, processing element 220 reduces the amplitude of focal sample 510 to an amplitude corresponding to an interpolated point 540 on a line 545 connecting median samples 530, 535.

In some embodiments, processing element 220 reduces the amplitude of focal samples to an amplitude between earlier and later median samples through a technique other than linear interpolation, such as nonlinear (e.g. higher order) interpolation or by computing an average amplitude from the amplitudes of the earlier and later median samples.

Figure 6:
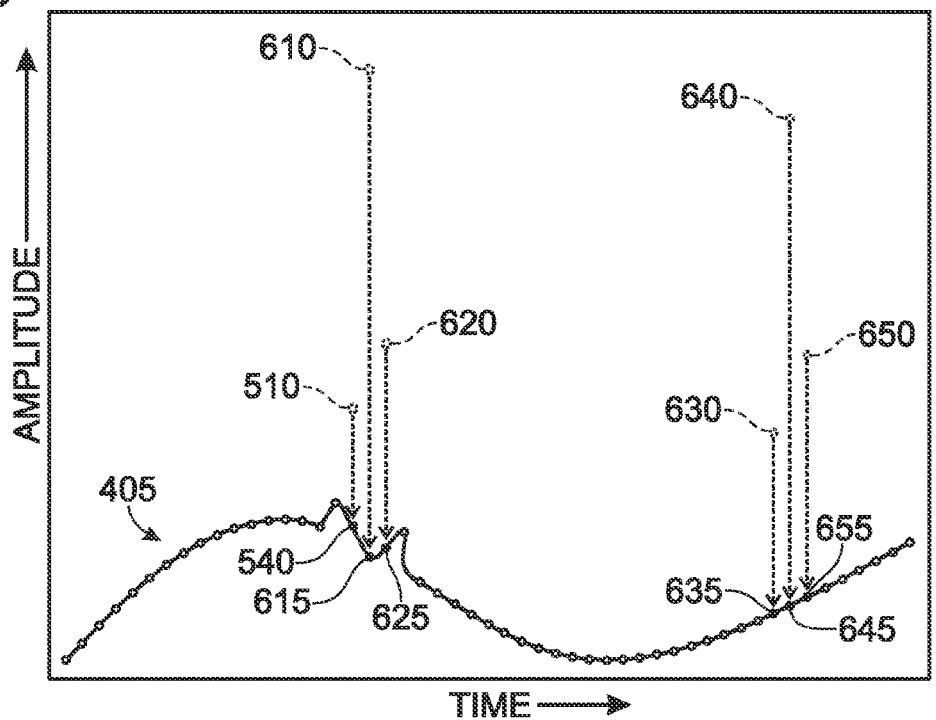
FIG. 6 illustrates further reductions of focal sample amplitudes in the waveform of FIG. 4 to reduced focal sample amplitudes pursuant to application of the method to the waveform in the first iteration.

The focus moves from left to right on the buffered waveform, one sample at a time, until the focus reaches the latest sample that permits a later sample group to be formed. For each focal sample, an individual determination is made as to whether to reduce the amplitude of the focal sample to an amplitude linearly interpolated from amplitudes of median samples of its identified earlier and later sample groups. After application of the method to the buffered waveform in a first iteration, the amplitudes of numerous focal samples that are part of noise spikes may be reduced to amplitudes corresponding to linearly interpolated points. For example, referring to FIG. 6, after performing the noise suppression method on buffered waveform 405 in a first iteration, initial amplitudes of focal samples 510, 610, 620, 630, 640, 650 are reduced to reduced amplitudes corresponding to linearly interpolated points 540, 615, 625, 635, 645, 655, respectively.

Figure 7:
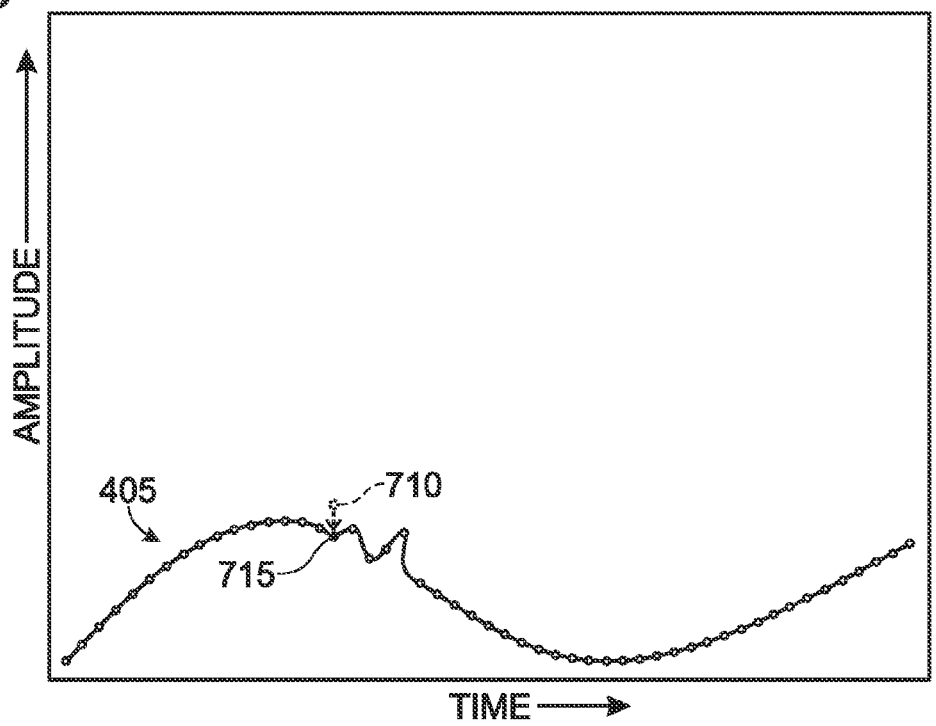
FIG. 7 illustrates a further reduction of a focal sample amplitude in the waveform of FIG. 4 to a reduced focal sample amplitude pursuant to application of the method to the waveform in a second iteration.
Figure 8:
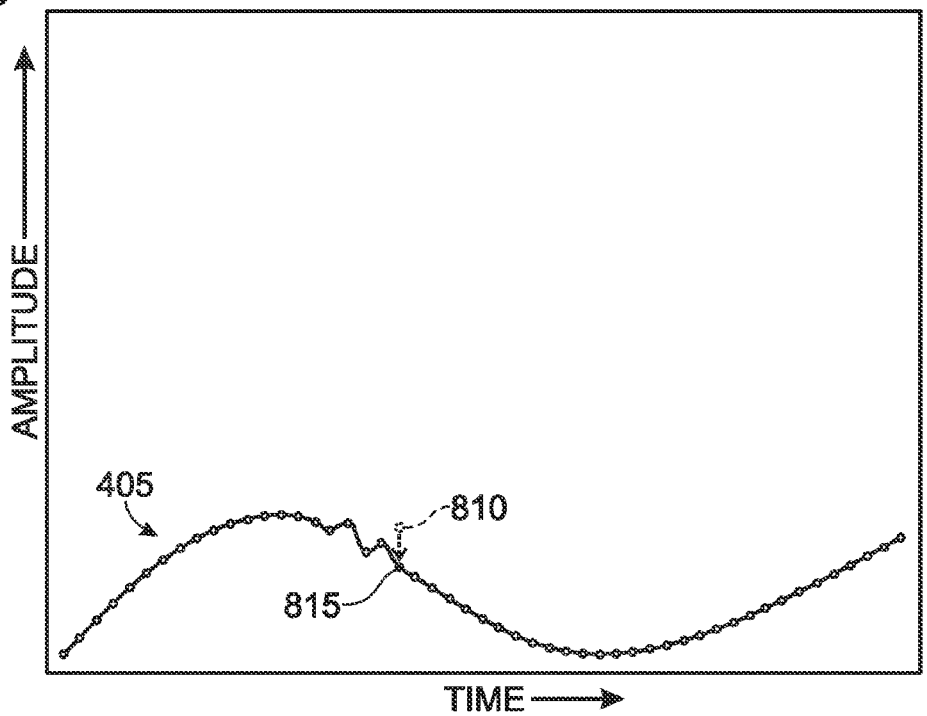
FIG. 8 illustrates a further reduction of a focal sample amplitude in the waveform of FIG. 4 to a reduced focal sample amplitude pursuant to application of the method to the waveform in a third iteration.

If a further iteration is indicated after applying the method to the buffered waveform in the current iteration, the focus returns to the initial focal sample of the buffered waveform and the method is repeated using a left-to-right focus shift to focus one-at-a-time on samples having a sufficient number of earlier and later samples to form earlier and later sample groups. For example, referring to FIG. 7, application of the method to buffered waveform 405 in a second iteration results in focal sample 710 being reduced to an amplitude corresponding to linearly interpolated point 715. And referring to FIG. 8, application of the method to buffered waveform 405 in a third iteration results in focal sample 810 being reduced to an amplitude corresponding to linearly interpolated point 815. It bears noting that focal sample amplitude reductions are integrated after the current iteration is completed and before the next iteration commences, such that all subsequent iterations of the method on the buffered waveform use the new amplitudes. The number of iterations performed on a buffered waveform is configurable. In some embodiments, the number of iterations is set equal to the number of samples in the current sample group or a multiple thereof. In other embodiments, the number of iterations is set to one. It will be appreciated that the number of iterations involves tradeoffs between adequate noise suppression and signal quality degradation, although a significant advantage of the present invention is preserving high signal quality even after a large number of iterations.

If a further iteration is not indicated after applying the method to the buffered waveform in the current iteration, processing element 220 extracts parametric data from the buffered waveform and outputs the data to output interface 230. Processing element 220 then replaces the buffered waveform in the signal buffer with the next energy waveform having the configurable number of digital samples. In some embodiments, consecutively buffered waveforms partially overlap so that buffered samples which are not selectable as focal samples in one waveform (due to being sufficiently close to a boundary of the buffered waveform to prevent formation of an earlier group) are selectable as focal samples in an immediately following buffered waveform.

In some embodiments, processing element 220 subjects acoustic signal waveforms to a low-pass filter to further suppress noise spikes.

Figure 9:
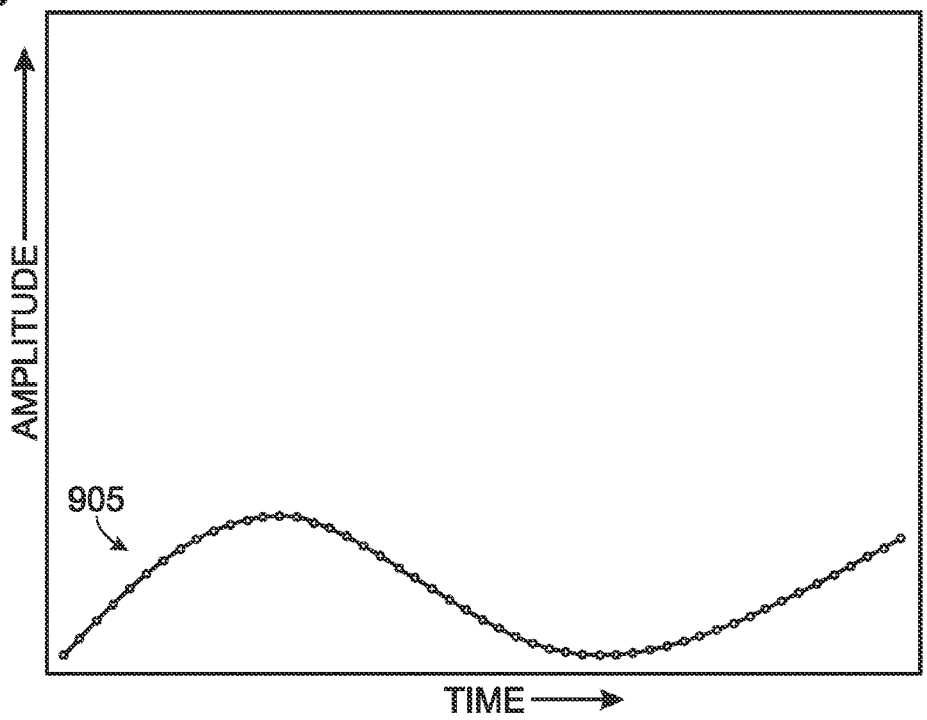
FIG. 9 illustrates identification of earlier, current and later sample groups in a non-noisy acoustic signal waveform based on a focal sample.

As mentioned above, a significant advantage of the present invention is in preserving high signal quality of waveforms even after applying the noise suppression method in a large number of iterations. In some embodiments, the present invention avoids large-scale degradation of signal quality of waveforms by conditioning application of the noise suppression method on the slope check of Step 325. However, even in embodiments where the slope check is not performed or the threshold used in the slope check is injudiciously set, the present invention preserves high signal quality relative to many conventional narrow band low-pass filtering or median filtering methods. This advantage of the present invention may be better understood by reference to FIGS. 9-11. FIG. 9 shows a non-noisy buffered waveform 905 that does not exhibit noise spikes requiring suppression and on which the present noise suppression method is performed. Referring to FIG. 10, after applying the present method to the buffered waveform in a first iteration (even without performing the slope check of Step 325), amplitudes of three samples 1005 are only nominally reduced and high signal quality is preserved. Referring to FIG. 11, even after applying the present method to the buffered waveform in a third iteration (without performing the slope check of Step 325 in any of the three iterations), amplitudes of five samples 1105 are only nominally reduced and high signal quality is maintained.

While the noise suppression technique of the present invention has been described as operating on an acoustic signal waveform in an acoustic monitoring system, the technique may be applied to other types of signal waveforms in other types of monitoring systems. For example, the noise suppression technique may be applied to suppress noise in various types of non-acoustic signal waveforms carrying respiration cycle information, such as an expired $CO_2$ waveform from a nasal cannula, an air pressure at mouth waveform from a pressure mask, an air temperature at mouth or nose waveform from a temperature sensor, a chest movement waveform from a video camera, or a chest movement waveform from a radar detector.

Moreover, while the noise suppression technique of the present invention has been described as operating on an energy waveform whose amplitude is positive across the entire waveform, the technique may be readily extended to bipolar waveforms by examining the absolute value of the focal sample amplitude relative to the absolute value of the discrete earlier sample amplitude and the discrete later sample amplitude. An exemplary method for suppressing noise events in a bipolar signal waveform having a plurality of samples comprises acquiring by a monitoring system the waveform; selecting by the monitoring system from the plurality of samples a focal sample; determining algorithmically by the monitoring system from the plurality of samples a discrete sample earlier than the focal sample and a discrete sample later than the focal sample that are noncontiguous with the focal sample; determining by the monitoring system an absolute value of an initial amplitude of the focal sample, an absolute value of an amplitude of the discrete earlier sample and an absolute value of an amplitude of the discrete later sample; determining by the monitoring system whether the absolute value of the initial focal sample amplitude is greater than the absolute value of the discrete earlier sample amplitude and greater than the absolute value of the discrete later sample amplitude; changing by the monitoring system the initial focal sample amplitude to a modified focal sample amplitude between the earlier and later sample amplitudes in response to determining that the absolute value of the initial focal sample amplitude is greater than the absolute values of the earlier and later sample amplitudes; and outputting by the monitoring system data determined using the waveform.

It will be appreciated by those of ordinary skill in the art, therefore, that the invention can be embodied in other specific forms without departing from the spirit or essential character hereof. The present description is considered in all respects to be illustrative and not restrictive. The scope of the invention is indicated by the appended claims, and all changes that come within the meaning and range of equivalents thereof are intended to be embraced therein.

What is claimed is:

1. A method for suppressing noise events in a signal waveform having a plurality of samples, comprising:
   acquiring by a monitoring system the waveform;
   selecting by the monitoring system from the plurality of samples a focal sample;
   determining algorithmically by the monitoring system from the plurality of samples a discrete sample earlier than the focal sample and a discrete sample later than the focal sample that are noncontiguous with the focal sample;
   determining by the monitoring system whether the focal sample has an initial amplitude greater than an amplitude of the discrete earlier sample and greater than an amplitude of the discrete later sample;
   reducing by the monitoring system the initial focal sample amplitude to a reduced focal sample amplitude between the earlier and later sample amplitudes in response to determining that the initial focal sample amplitude is greater than the earlier and later sample amplitudes, and
   outputting by the monitoring system data determined using the waveform;
   wherein the first determining step comprises identifying a current sample group consisting of the focal sample, one or more samples earlier than the focal sample that are contiguous with the focal sample and one or more samples later than the focal sample that are contiguous with the focal sample;
   identifying an earlier sample group consisting of the discrete earlier sample and two or more additional samples that are earlier than the current sample group;
   identifying a later sample group consisting of the discrete later sample and two or more additional samples that are later than the current sample group;
   determining that the discrete earlier sample is a median amplitude sample of the earlier sample group; and
   determining that the discrete later sample is a median amplitude sample of the later sample group.

2. The method of claim 1, wherein the earlier, current and later sample groups each consist of an odd number of samples.

3. The method of claim 1, wherein the earlier, current and later sample groups consist of a number of samples selected to correspond with a predetermined target width of noise spikes to be suppressed.

4. The method of claim 1, further comprising determining by the monitoring system that a slope between at least two consecutive samples within one or more of the earlier, current or later sample group exceeds a configurable threshold.

5. The method of claim 1, wherein the reduced focal sample amplitude is linearly interpolated from the earlier sample amplitude and the later sample amplitude.

6. The method of claim 1, wherein the reduced focal sample amplitude is nonlinearly interpolated from the earlier sample amplitude and the later sample amplitude.

7. The method of claim 1, wherein the reduced focal sample amplitude is computed as an average of the earlier sample amplitude and the later sample amplitude.

8. The method of claim 1, further comprising, after the reducing step, selecting by the monitoring system other samples within the plurality of samples of the waveform as the focal sample and performing by the monitoring system at least the determining steps for the other samples as the focal sample.

9. The method of claim 1, further comprising
reselecting by the monitoring system each of the samples within the plurality of samples of the waveform as the focal sample and reperforming by the monitoring system at least the determining steps for each of the samples as the focal sample.

10. The method of claim 1, wherein the signal waveform is an acoustic signal waveform.

11. The method of claim 1, wherein the outputted data comprise respiration data.

12. The method of claim 1, wherein the outputted data comprise heart data.

13. A monitoring system, comprising:
a signal capture element configured to acquire a signal waveform comprising a plurality of samples;
a signal processing element operatively coupled with the capture element and configured to select from the plurality of samples a focal sample, determine algorithmically from the plurality of samples a discrete sample earlier than the focal sample and a discrete sample later than the focal sample that are noncontiguous with the focal sample, determine whether the focal sample has an initial amplitude greater than an amplitude of the discrete earlier sample and greater than an amplitude of the discrete later sample and reduce the initial focal sample amplitude to a reduced focal sample amplitude between the earlier and later sample amplitudes in response to determining that the initial focal sample amplitude is greater than the earlier and later sample amplitudes; and
a data output interface operatively coupled with the processing element and configured to output data determined using the waveform;
wherein the processing element is configured to identify a current sample group consisting of the focal sample, one or more samples earlier than the focal sample that are contiguous with the focal sample and one or more samples later than the focal sample that are contiguous with the focal sample, identify an earlier sample group consisting of the discrete earlier sample and two or more additional samples that are earlier than the current sample group, identify a later sample group consisting of the discrete later sample and two or more additional samples that are later than the current sample group, determine that the discrete earlier sample is a median amplitude sample of the earlier sample group and determine that the discrete later sample is a median amplitude sample of the later sample group.

14. The monitoring system of claim 13, wherein the processing element is further configured to determine that a slope between at least two consecutive samples within one or more of the earlier, current or later sample groups exceeds a configurable threshold.

15. The monitoring system of claim 13, wherein the reduced focal sample amplitude is linearly interpolated from the earlier sample amplitude and the later sample amplitude.

16. The monitoring system of claim 13, wherein the signal waveform is an acoustic signal waveform.

17. A method for suppressing noise events in a bipolar signal waveform having a plurality of samples, comprising:
acquiring by a monitoring system the waveform;
selecting by the monitoring system from the plurality of samples a focal sample;
determining algorithmically by the monitoring system from the plurality of samples a discrete sample earlier than the focal sample and a discrete sample later than the focal sample that are noncontiguous with the focal sample;
determining by the monitoring system an absolute value of an initial amplitude of the focal sample, an absolute value of an amplitude of the discrete earlier sample and an absolute value of an amplitude of the discrete later sample;
determining by the monitoring system whether the absolute value of the initial focal sample amplitude is greater than the absolute value of the discrete earlier sample amplitude and greater than the absolute value of the discrete later sample amplitude;
changing by the monitoring system the initial focal sample amplitude to a modified focal sample amplitude between the earlier and later sample amplitudes in response to determining that the absolute value of the initial focal sample amplitude is greater than the absolute values of the earlier and later sample amplitudes, and
outputting by the monitoring system data determined using the waveform;
wherein the first determining step comprises identifying a current sample group consisting of the focal sample, one or more samples earlier than the focal sample that are contiguous with the focal sample and one or more samples later than the focal sample that are contiguous with the focal sample;
identifying an earlier sample group consisting of the discrete earlier sample and two or more additional samples that are earlier than the current sample group;
identifying a later sample group consisting of the discrete later sample and two or more additional samples that are later than the current sample group;
determining that the discrete earlier sample is a median amplitude sample of the earlier sample group; and
determining that the discrete later sample is a median amplitude sample of the later sample group.

* * * * *